United States Patent
Labrom et al.

(10) Patent No.: US 7,951,169 B2
(45) Date of Patent: May 31, 2011

(54) POSTERIOR DYNAMIC STABILIZATION CROSS CONNECTORS

(75) Inventors: Robert Labrom, Brisbane (AU); Amie Borgstrom, North Attleborough, MA (US); William Dunbar, Norton, MA (US); SeungKyu Daniel Kwak, Grafton, MA (US); John Riley Hawkins, Cumberland, RI (US); Missoum Moumene, Newton, MA (US); Ian Burgess, Barrington, RI (US); Lutz Biedermann, Villingen (DE); Wilfried Matthis, Weisweil (DE)

(73) Assignee: DePuy Spine, Inc., Raynham, MA (US)

( * ) Notice: Subject to any disclaimer, the term of this patent is extended or adjusted under 35 U.S.C. 154(b) by 418 days.

(21) Appl. No.: 11/160,142

(22) Filed: Jun. 10, 2005

(65) Prior Publication Data

US 2006/0282078 A1    Dec. 14, 2006

(51) Int. Cl.
*A61B 17/70* (2006.01)
(52) U.S. Cl. .......... 606/249; 606/248; 606/60; 606/246
(58) Field of Classification Search .............. 606/61, 606/246–279, 60; 403/132
See application file for complete search history.

(56) References Cited

U.S. PATENT DOCUMENTS

| | | | |
|---|---|---|---|
| 4,743,260 A | 5/1988 | Burton | |
| 4,998,936 A * | 3/1991 | Mehdian | 606/250 |
| 5,030,220 A * | 7/1991 | Howland | 606/261 |
| 5,084,049 A | 1/1992 | Asher et al. | |
| 5,092,866 A | 3/1992 | Breard | |
| 5,129,899 A | 7/1992 | Small et al. | |
| 5,133,716 A * | 7/1992 | Plaza | 606/250 |
| 5,282,863 A | 2/1994 | Burton | |
| 5,334,203 A * | 8/1994 | Wagner | 606/61 |
| 5,387,213 A | 2/1995 | Breard et al. | |
| 5,399,164 A | 3/1995 | Snoke et al. | |
| 5,413,576 A | 5/1995 | Rivard | |
| 5,415,661 A | 5/1995 | Holmes | |
| 5,474,086 A | 12/1995 | McCormick et al. | |
| 5,540,688 A | 7/1996 | Navas | |
| 5,556,431 A | 9/1996 | Buttner-Janz | |
| 5,562,737 A | 10/1996 | Graf | |
| 5,571,191 A | 11/1996 | Fitz | |
| 5,609,634 A | 3/1997 | Voydeville | |
| 5,611,800 A * | 3/1997 | Davis et al. | 606/250 |
| 5,645,599 A | 7/1997 | Samani | |
| 5,672,175 A | 9/1997 | Martin | |
| 5,702,395 A * | 12/1997 | Hopf | 606/250 |
| 5,702,452 A * | 12/1997 | Argenson et al. | 606/253 |
| 5,800,548 A * | 9/1998 | Martin et al. | 606/253 |
| 5,810,815 A * | 9/1998 | Morales | 606/250 |

(Continued)

FOREIGN PATENT DOCUMENTS

EP    0669109    2/1994

(Continued)

*Primary Examiner* — Thomas C Barrett
*Assistant Examiner* — Christine L Nelson
(74) *Attorney, Agent, or Firm* — Nutter McClennen & Fish LLP

(57) ABSTRACT

Various methods and devices are provided for stabilizing the posterior elements of the spine, and more preferably methods and devices are provided for sharing the load with the intervertebral disc, the facet joints, the ligaments, and the muscles of the spinal column. In certain exemplary embodiments, methods and devices are provided for substantially controlling or providing resistance to movement, e.g., flexion, extension, lateral bending, and/or axial rotation, of the adjacent vertebrae.

14 Claims, 11 Drawing Sheets

U.S. PATENT DOCUMENTS

| | | | |
|---|---|---|---|
| 5,865,846 A * | 2/1999 | Bryan et al. | 128/898 |
| 5,885,284 A * | 3/1999 | Errico et al. | 606/252 |
| RE36,221 E | 6/1999 | Breard et al. | |
| 5,961,516 A | 10/1999 | Graf | |
| 5,980,523 A | 11/1999 | Jackson | |
| 5,984,922 A | 11/1999 | McKay | |
| 5,989,250 A | 11/1999 | Wagner et al. | |
| RE36,758 E | 6/2000 | Fitz | |
| 6,132,464 A | 10/2000 | Martin | |
| 6,136,000 A * | 10/2000 | Louis et al. | 606/250 |
| 6,136,002 A * | 10/2000 | Shih et al. | 606/250 |
| 6,241,746 B1 | 6/2001 | Bosma et al. | |
| 6,248,106 B1 | 6/2001 | Ferree | |
| 6,267,764 B1 | 7/2001 | Elberg | |
| 6,273,888 B1 | 8/2001 | Justis | |
| 6,306,139 B1 | 10/2001 | Fuentes et al. | |
| 6,306,170 B2 | 10/2001 | Ray | |
| 6,419,703 B1 | 7/2002 | Fallin | |
| 6,428,106 B1 | 8/2002 | Andersson | |
| 6,440,169 B1 | 8/2002 | Elberg et al. | |
| 6,514,255 B1 | 2/2003 | Ferree | |
| 6,554,831 B1 | 4/2003 | Rivard et al. | |
| 6,565,605 B2 | 5/2003 | Goble | |
| 6,579,319 B2 | 6/2003 | Goble | |
| 6,589,243 B1 | 7/2003 | Viart et al. | |
| 6,610,091 B1 | 8/2003 | Reiley | |
| 6,626,909 B2 * | 9/2003 | Chin | 606/276 |
| 6,645,207 B2 | 11/2003 | Dixon | |
| 6,669,729 B2 | 12/2003 | Chin | |
| 6,761,720 B1 | 7/2004 | Senegas | |
| 6,783,526 B1 * | 8/2004 | Lin et al. | 606/61 |
| 6,811,567 B2 | 11/2004 | Reiley | |
| 6,949,123 B2 | 9/2005 | Reiley | |
| 6,966,910 B2 | 11/2005 | Ritland | |
| 6,974,478 B2 | 12/2005 | Reiley et al. | |
| 7,011,685 B2 | 3/2006 | Arnin et al. | |
| 7,052,515 B2 | 5/2006 | Simonson | |
| 7,125,410 B2 | 10/2006 | Freudiger | |
| 7,189,234 B2 | 3/2007 | Zucherman et al. | |
| 7,261,738 B2 | 8/2007 | Casey | |
| 7,282,065 B2 | 10/2007 | Kirschman | |
| 7,291,150 B2 | 11/2007 | Graf | |
| 7,294,129 B2 | 11/2007 | Hawkins et al. | |
| 7,338,527 B2 | 3/2008 | Blatt et al. | |
| 7,361,196 B2 | 4/2008 | Fallin et al. | |
| 2002/0055740 A1 | 5/2002 | Lieberman | |
| 2002/0065557 A1 | 5/2002 | Goble et al. | |
| 2002/0072800 A1 | 6/2002 | Goble et al. | |
| 2002/0123806 A1 | 9/2002 | Reiley | |
| 2002/0133155 A1 | 9/2002 | Ferree | |
| 2002/0143331 A1 | 10/2002 | Zucherman et al. | |
| 2003/0004572 A1 | 1/2003 | Goble et al. | |
| 2003/0028250 A1 * | 2/2003 | Reiley et al. | 623/17.11 |
| 2003/0055427 A1 | 3/2003 | Graf | |
| 2003/0083657 A1 | 5/2003 | Drewry | |
| 2003/0109880 A1 | 6/2003 | Shirado et al. | |
| 2003/0135277 A1 | 7/2003 | Bryan et al. | |
| 2003/0153912 A1 | 8/2003 | Graf | |
| 2003/0171749 A1 | 9/2003 | Le Couedic et al. | |
| 2003/0171750 A1 | 9/2003 | Chin | |
| 2003/0187508 A1 | 10/2003 | Cauthen | |
| 2003/0191470 A1 | 10/2003 | Ritland | |
| 2003/0191532 A1 | 10/2003 | Goble et al. | |
| 2003/0220642 A1 | 11/2003 | Freudiger | |
| 2003/0220643 A1 | 11/2003 | Ferree | |
| 2004/0002708 A1 | 1/2004 | Ritland | |
| 2004/0006391 A1 | 1/2004 | Reiley | |
| 2004/0015166 A1 | 1/2004 | Gorek | |
| 2004/0049189 A1 | 3/2004 | Le Couedic et al. | |
| 2004/0049190 A1 | 3/2004 | Biedermann et al. | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049281 A1 | 3/2004 | Reiley | |
| 2004/0073215 A1 | 4/2004 | Carli | |
| 2004/0111154 A1 | 6/2004 | Reiley | |
| 2004/0116927 A1 | 6/2004 | Graf | |
| 2004/0133203 A1 | 7/2004 | Young et al. | |
| 2004/0143264 A1 | 7/2004 | McAfee | |
| 2004/0147928 A1 | 7/2004 | Landry et al. | |
| 2004/0186475 A1 | 9/2004 | Falahee | |
| 2004/0225289 A1 | 11/2004 | Biedermann et al. | |
| 2004/0236329 A1 | 11/2004 | Panjabi | |
| 2004/0243239 A1 | 12/2004 | Taylor | |
| 2005/0033431 A1 | 2/2005 | Gordon et al. | |
| 2005/0033432 A1 | 2/2005 | Gordon et al. | |
| 2005/0033439 A1 | 2/2005 | Gordon et al. | |
| 2005/0055098 A1 | 3/2005 | Zdeblick et al. | |
| 2005/0065514 A1 | 3/2005 | Studer | |
| 2005/0101954 A1 | 5/2005 | Simonson | |
| 2005/0101956 A1 | 5/2005 | Simonson | |
| 2005/0102028 A1 | 5/2005 | Arnin et al. | |
| 2005/0113927 A1 | 5/2005 | Malek | |
| 2005/0171539 A1 | 8/2005 | Braun et al. | |
| 2005/0203512 A1 | 9/2005 | Hawkins et al. | |
| 2005/0216081 A1 | 9/2005 | Taylor | |
| 2005/0261768 A1 | 11/2005 | Trieu | |
| 2005/0267579 A1 | 12/2005 | Reiley et al. | |
| 2006/0015181 A1 | 1/2006 | Elberg | |
| 2006/0106381 A1 | 5/2006 | Ferree et al. | |
| 2006/0149238 A1 * | 7/2006 | Sherman et al. | 606/61 |
| 2006/0217723 A1 | 9/2006 | Suh | |
| 2006/0282075 A1 | 12/2006 | Labrom et al. | |
| 2006/0282076 A1 | 12/2006 | Labrom et al. | |
| 2006/0282077 A1 | 12/2006 | Labrom et al. | |
| 2006/0282078 A1 | 12/2006 | Labrom et al. | |
| 2006/0282079 A1 | 12/2006 | Labrom et al. | |
| 2008/0097446 A1 * | 4/2008 | Reiley et al. | 606/69 |

FOREIGN PATENT DOCUMENTS

| | | |
|---|---|---|
| WO | WO-01/45576 | 6/2001 |
| WO | WO-02/17803 | 3/2002 |
| WO | WO-02/43603 | 6/2002 |
| WO | WO-02/102259 | 12/2002 |
| WO | WO-03/007828 | 1/2003 |
| WO | WO-03/009737 | 2/2003 |
| WO | WO-2004/024011 | 3/2004 |
| WO | WO-2004/034916 | 4/2004 |
| WO | 2005044123 A1 | 5/2005 |

* cited by examiner

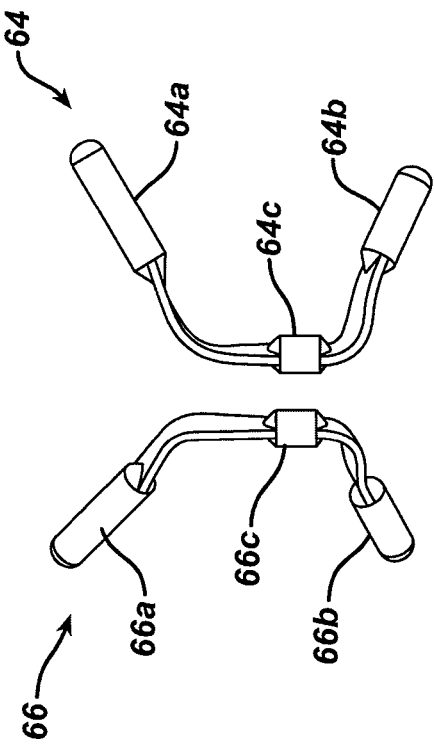
FIG. 6B
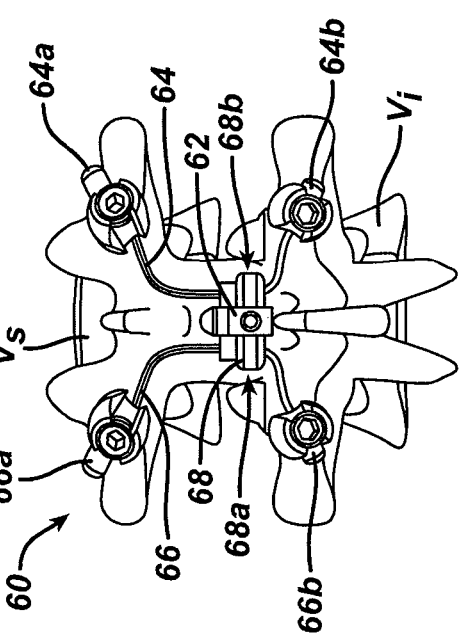
FIG. 6A
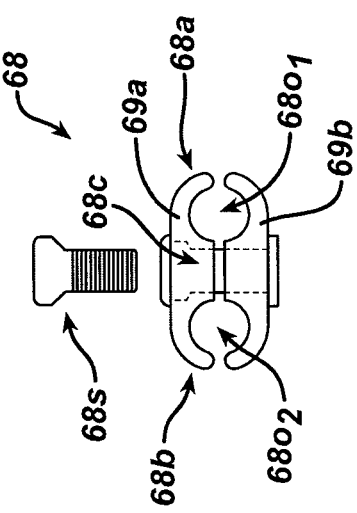
FIG. 6D
FIG. 6C

POSTERIOR DYNAMIC STABILIZATION CROSS CONNECTORS

BACKGROUND OF THE INVENTION

The vertebrae in a patient's spinal column are linked to one another by the disc and the facet joints, which control movement of the vertebrae relative to one another. Each vertebra has a pair of articulating surfaces located on the left side, and a pair of articulating surfaces located on the right side, and each pair includes a superior articular surface, which faces upward, and an inferior articular surface, which faces downward. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. Damaged, diseased levels in the spine were traditionally fused to one another. While such a technique may relieve pain, it effectively prevents motion between at least two vertebrae. As a result, additional stress may be applied to the adjoining levels, thereby potentially leading to further damage.

More recently, techniques have been developed to restore normal function to the facet joints. One such technique involves covering the facet joint with a cap to preserve the bony and articular structure. Capping techniques, however, are limited in use as they will not remove the source of the pain in osteoarthritic joints. Caps are also disadvantageous as they must be available in a variety of sizes and shapes to accommodate the wide variability in the anatomical morphology of the facets. Caps also have a tendency to loosen over time, potentially resulting in additional damage to the joint and/or the bone support structure containing the cap.

Other techniques for restoring the normal function to the posterior element involve arch replacement, in which superior and inferior prosthetic arches are implanted to extend across the vertebra typically between the spinous process. The arches can articulate relative to one another to replace the articulating function of the facet joints. One drawback of current articulating facet replacement devices, however, is that they require the facet joints to be resected. Moreover, alignment of the articulating surfaces with one another can be challenging.

Accordingly, there remains a need for improved systems and methods that are adapted to mimic the natural function of the facet joints.

BRIEF SUMMARY OF THE INVENTION

The present invention provides various methods and devices for stabilizing the posterior elements of the spine. In certain exemplary embodiments, methods and devices are provided for controlling or providing resistance to movement, e.g., flexion, extension, lateral bending, and/or axial rotation, at least two adjacent vertebrae. In certain exemplary embodiments, the methods and devices are particularly advantageous in assisting the facet joints and posterior spinal muscles and ligaments in controlling motion in the lumbar spine, either with a deranged intact disc, with a nucleus replacement, or with a total disc replacement.

In one exemplary embodiment, a spinal stabilization device is provided having a central spacer with at least two arms extending therefrom and adapted to couple to adjacent vertebrae. The central spacer and the arms can have a unitary configuration and can be formed from an elastomeric material with multiple durometers. For example, a first portion of each arm adjacent to the central spacer can have a durometer that is less than a durometer of the central spacer, and a terminal portion of each arm can have a durometer that is greater than a durometer of the central spacer. In one exemplary embodiment, the terminal portion of each arm is substantially rigid to allow the arms to be coupled to vertebrae.

In another exemplary embodiment, a spinal stabilization device is provided having a central spacer that is adapted to be positioned between posterior elements of adjacent vertebrae and that is adapted to limit extension of the adjacent vertebrae. The device can also include at least one pair of arms extending from opposed sides of the central spacer and adapted to couple to a vertebra. At least a portion of the at least one pair of arms can be pliable to control or provide resistance to movement, e.g., flexion, extension, lateral bending, and/or axial rotation, of adjacent vertebrae coupled thereto. The arms and the central spacer can be of a unitary construction, or they can be fixedly or removably coupled to one another. For example, in one embodiment at least one of the arms can be slidably disposed through the central spacer.

In another embodiment, the pair of arms can have a first portion adjacent to the central spacer and a second terminal end portion. The first portion can be more pliable than the second terminal end portion to allow flexion of the adjacent vertebrae. Pliability, e.g., flexibility, elasticity, etc., can be provided by, for example, a coiled portion formed on the arms. In another embodiment, the at least one pair of arms can be in the form of first and second arms extending from opposed sides of the central spacer, a third arm removably coupled to the first arm, and a fourth arm removably coupled to the second arm.

In another exemplary embodiment, the spinal stabilization device can include a first pair of arms extending from a first lateral side of the central spacer and a second pair of arms extending from a second lateral side of the central spacer. The first pair of arms can be integrally formed within one another, and a second pair of arms integrally formed with one another. In use, the first and second pair of arms can be adapted to mate to the central spacer at a variety of angular orientations.

In other aspects, a spinal stabilization device is provided having a first pair of arms and a second pair of arms. Each pair of arms can have a superior portion adapted to mate to a superior vertebra, an inferior portion adapted to mate to an inferior vertebra, and a central portion extending between the superior and inferior portions. The device can also include a central spacer that is adapted to be positioned between posterior elements of adjacent vertebrae, and that includes a cross-connector extending therethrough and adapted to engage the central portion of the first and second pair of arms. In an exemplary embodiment, the cross-connector is slidably adjustable relative to the first and second pair of arms. The cross-connector can have a variety of configurations, and it can include, for example, hook-shaped members formed on opposed ends thereof and adapted to engage the central portion of the first and second pair of arms. Alternatively, the cross-connector can be in the form of a clamp having openings formed in opposed ends thereof for receiving the central portion of the first and second pair of arms and for engaging the arms when the clamp is in a closed position.

In use, the first pair of arms extending from the central spacer can be coupled to a first lateral side of adjacent superior and inferior vertebrae, and the second pair of arms extending from the central spacer can be coupled to a second lateral side of adjacent superior and inferior vertebrae. The central spacer can then be slid in superior-inferior direction relative to the first and second arms to position the central spacer as desired. Once properly position, the central spacer can be locked in a fixed position relative to the first and second pair of arms.

In other aspects, the spinal stabilization device can include a first pair of arms extending from the first lateral side of the central spacer and adapted to couple to adjacent superior and inferior vertebrae, and a second pair of arms extending from the second lateral side of the central spacer and adapted to couple to adjacent superior and inferior vertebrae. At least a portion of at least one of the first and second pair of arms can be pliable to control or provide resistance to movement, e.g., flexion, extension, lateral bending, and/or axial rotation, of adjacent superior and inferior vertebrae coupled thereto. While the first and second pair of arms can have a variety of configurations, in one exemplary embodiment, the first pair of arms can be coupled to one another and the second pair of arms can be coupled to one another, and the first and second pair of arms can be removably mated to the central spacer. In another exemplary embodiment, the first pair of arms can comprise a first arm and a second arm, and the second pair of arms can comprise a third arm and a fourth arm, and the first, second, third, and fourth arms can be independently removably mated to the central spacer. The central spacer can include a first opening formed in the first lateral side and adapted to removably receive the first and second arms, and a second opening formed in the second, opposed lateral side and adapted to removably receive the third and fourth arms. First and second locking mechanisms can be disposed through the first and second openings for locking the first, second, third, and fourth arms to the central spacer.

In another exemplary embodiment, a multi-level spinal stabilization system is provided. The system can include at least two X-shaped members, and each X-shaped member can have a central member with a superior pair of arms extending from opposed lateral sides thereof and an inferior pair of arms extending from the opposed lateral sides thereof. The superior pair of arms of a first X-shaped member can be coupled to an inferior pair of arms of a second X-shaped member. In one embodiment, the at least two X-shaped members can be of a unitary construction and can, for example, be formed from a polymeric material. In certain exemplary embodiments, the X-shaped members can have multiple durometers. In other embodiments, the multi-level spinal stabilization system can include first and second connectors that are adapted to couple the superior pair of arms of the first X-shaped member to the inferior pair of arms of the second X-shaped member. The first and second connectors can be, for example, first and second plates pivotally coupled to one another. Each plate can be adapted to engage a terminal end of one arm of the superior and inferior pair of arms. In another embodiment, the first and second connectors can be in the form of a clamp mechanism that is adapted to engage a terminal end of one of the superior pair of arms and a terminal end of one of the inferior pair of arms.

In yet another aspect, an exemplary method for stabilizing multiple adjacent vertebrae is provided and includes coupling an implant to a posterior portion of at least three adjacent vertebrae. The implant can have a unitary configuration and it can be formed from an elastomeric material with multiple durometers to allow the implant to provide resistance to movement of the adjacent vertebrae.

In another exemplary embodiment, a method for stabilizing multiple adjacent vertebrae is provided and includes positioning a central spacer of a first X-shaped member between posterior elements of a first vertebra and an adjacent second vertebra, coupling opposed superior arms of the first X-shaped member to the first vertebra, coupling opposed inferior arms of the first X-shaped member to the second vertebra, positioning a central spacer of a second X-shaped member between posterior elements of the second vertebra and an adjacent third vertebra, the second X-shaped member having opposed superior arms that are coupled to the opposed inferior arms of the first X-shaped member, and coupling opposed inferior arms of the second X-shaped member to the third vertebra.

In other aspects, a spinal stabilization device is provided having a central spacer with opposed arms coupled to opposed lateral sides thereof. Each arm can have a first portion that is adapted to couple to a first vertebra, and a second portion that is adapted to be positioned adjacent to a spinous process of a second adjacent vertebra such that the opposed arms are adapted to control or provide resistance to movement, e.g., flexion, extension, lateral bending, and/or axial rotation, of first and second adjacent vertebrae. In one exemplary embodiment, the second portion of the first arm can be coupled to the second portion of the second arm to form a U-shaped member that is adapted to be positioned around the spinous process of a second adjacent vertebra. The U-shaped member can be fixedly coupled to the central spacer. The opposed arms can have a variety of other configurations. For example, they can be integrally formed with the central spacer. In other embodiments the opposed arms can be substantially pliable, and can include, for example, a coil-shaped region.

In other aspects, a spinal stabilization device is provided having a central spacer that is adapted to be positioned between posterior elements of adjacent superior and inferior vertebrae. Opposed first and second arms can be coupled to opposed lateral sides of the central spacer. Each arm can include a superior portion that extends in a superior direction from the central spacer and that is adapted to be coupled to a superior vertebra. The superior portion of the first arm and the superior portion of the second arm can diverge with respect to one another from the central spacer. Each arm can also include an inferior portion that extends in an inferior direction from the central spacer. The inferior portion of each arm can extend substantially parallel to one another such that the inferior portion of the first arm and the inferior portion of the second arm is adapted to engage a spinous process of an inferior vertebra therebetween to substantially control or provide resistance to movement, e.g., flexion, extension, lateral bending, and/or axial rotation, of adjacent superior and inferior vertebrae. In one exemplary embodiment, the superior portion of each of the first and second arms is curved. In another embodiment, the inferior portion of the first and second arms are coupled to one another to form a U-shaped member that is adapted to extend around a spinous process of an inferior vertebrae.

Exemplary methods for stabilizing adjacent vertebrae are also provided, and in one embodiment the method can include positioning a central spacer between the posterior elements of first and second adjacent vertebrae. The central spacer can be adapted to substantially limit extension of the first and second adjacent vertebrae. The method can also include positioning a first arm adjacent to a first lateral side of the central spacer such that a first portion of the first arm is positioned adjacent to the first vertebra and a second portion of the first arm is positioned adjacent to the spinous process of the second vertebra, and positioning a second arm adjacent to a second, opposed lateral side of the central spacer such that a first portion of the second arm is positioned adjacent to the first vertebra and a second portion of the second arm is positioned adjacent to the spinous process of the second vertebra. The second portions of the first and second arms can substantially control or provide resistance to movement, e.g., flexion, extension, lateral bending, and/or axial rotation of the first and second adjacent vertebrae. In one exemplary embodiment, the second portions of the first and second arms can be coupled to one another to form a substantially U-shaped member, and the U-shaped member can be around the spinous process of the second vertebra. In another exemplary embodiment, the first arm can be coupled to the first lateral side of the central spacer, and the second arm can be coupled to the second, opposed lateral side of the central spacer. The second portions of the first and second arms can engage opposed sides of the spinous process of the second vertebra.

Another exemplary method for stabilizing adjacent vertebrae can include positioning a central spacer of a stabilization device between posterior elements of adjacent vertebrae, and attaching arms extending from opposed sides of the central spacer to at least one of the adjacent vertebrae. The stabilization device can be adapted to control or provide resistance to movement, e.g., flexion, extension, lateral bending, and/or axial rotation, of the adjacent vertebrae. In one exemplary embodiment, attaching arms extending from opposed sides of the central spacer to at least one of the adjacent vertebrae can include attaching a first pair of arms extending from the central spacer to a superior vertebra, and attaching a second pair of arms extending from the central spacer to an inferior vertebra. The first and second pair of arms can be pivotally coupled to the central spacer to allow rotational movement of the central spacer between the posterior elements of the superior and inferior vertebrae. At least a portion of at least one of the first and second pairs of arms can be pliable to control or provide resistance to movement, e.g., flexion, extension, lateral bending, and/or axial rotation, of the adjacent vertebrae. In another embodiment, attaching arms extending from opposed sides of the central spacer to at least one of the adjacent vertebrae can include attaching a first portion of a first arm to a first vertebra and attaching a first portion of a second arm to the first vertebra. A second portion of each of the first and second arms can engage a spinous process of a second vertebra that is adjacent to the first vertebra.

In yet another exemplary embodiment, a method for stabilizing adjacent vertebrae is provided and includes determining a required amount of spacing between posterior elements of adjacent vertebrae based on a tension of a ligament extending between the posterior elements, positioning a central spacer having a height that corresponds to the required amount of space determined between the posterior elements of the adjacent vertebrae, and attaching arms extending from opposed sides of the central spacer to at least one of the adjacent vertebrae.

In another exemplary embodiment, a method for stabilizing adjacent vertebrae can include implanting a nucleus replacement between adjacent superior and inferior vertebrae, and coupling an implant to a posterior portion of at least one of the superior and inferior vertebrae such that the implant is adapted to offload the nucleus replacement during axial rotation of the adjacent superior and inferior vertebrae.

BRIEF DESCRIPTION OF THE DRAWINGS

The invention will be more fully understood from the following detailed description taken in conjunction with the accompanying drawings, in which:

FIG. 6A is a posterior view of a portion of a human spinal column having a spinal stabilization device implanted therein and having a central spacer adjustably coupled to opposed arms in accordance with yet another exemplary embodiment;

FIG. 6B is a perspective view of the opposed arms of the device shown in FIG. 6A;

FIG. 6C is a partially transparent side view of the cross-connector of the device shown in FIG. 6A;

FIG. 6D is a partially transparent side view of another embodiment of a cross-connector for use with the device shown in FIG. 6A;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for stabilizing the posterior elements of the spine, and more preferably methods and devices are provided for sharing the load with the intervertebral disc, the facet joints, the ligaments, and the muscles of the spinal column. The methods and devices can also stabilize and protect the facet joints in the lumbar spine, as well as other posterior spinal muscles and ligaments. The methods are devices can be used with the natural disc or with an artificial disc replacement. In certain exemplary embodiments, the methods and devices can be adapted to substantially control or provide resistance to movement of at least two adjacent vertebrae. The movement can include any one or a combination of flexion, extension, lateral bending, and/or axial rotation or at least two adjacent vertebrae. The methods and devices can also be adapted for minimally invasive use. A person skilled in the art will appreciate that the particular devices and methods disclosed herein can be used for a variety of other medical purposes.

Figure 1A:
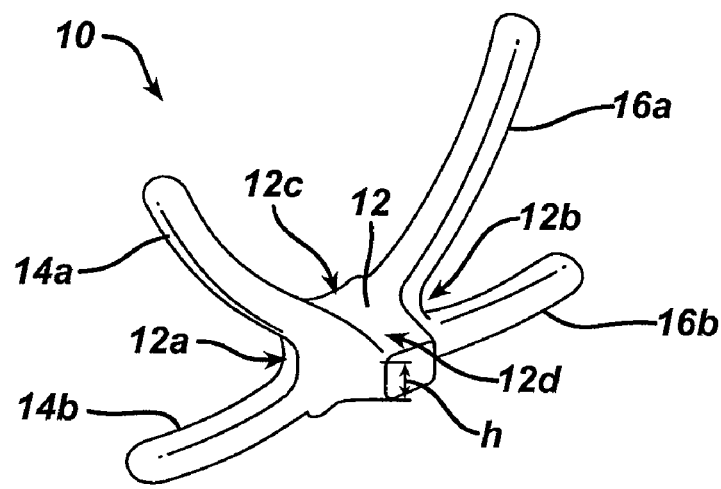
FIG. 1A is a perspective view of one exemplary embodiment of a spinal stabilization device having a unitary construction.

FIG. 1A illustrates one exemplary embodiment of a spinal stabilization device 10. As shown, the device 10 is substantially X-shaped and is of a unitary construction. In particular, the exemplary device 10 includes a central spacer 12 that is adapted to be disposed between posterior elements of two adjacent vertebrae, and two pairs of arms 14a, 14b, 16a, 16b that extend from each lateral side 12a, 12b of the central spacer 12, such that the device 10 has a total of four arms 14a, 14b, 16a, 16b. Two of the arms, i.e., the superior arms 14a, 16a, extend in a superior direction from the central spacer 12 to couple to a vertebra that is positioned superior to the central spacer 12. The other two arms, i.e., the inferior arms 14b, 16b, can extend laterally outward, or they can extend in an inferior direction, from the central spacer 12 to couple to a vertebra that is inferior to the central spacer 12.

The central spacer 12 can have variety of configurations, but in one exemplary embodiment, the central spacer 12 has a shape and size that allows the central spacer 12 to be positioned between two posterior elements, such as the spinous processes, of two adjacent vertebrae and that is adapted to limit or prevent extension of the adjacent vertebrae. As shown in FIG. 1A, the exemplary central spacer 12 is substantially wedge-shaped and has an anterior portion 12c that is substantially square or rectangular in shape, and a posterior portion 12d that has a height h that tapers or decreases in a posterior direction to form a wedge. Such a configuration allows the central spacer 12 to be positioned between two spinous processes of two adjacent vertebrae and to substantially limit of prevent extension of the vertebrae relative to one another. The central spacer 12 can have a variety of other shapes and sizes including, by way of non-limiting example, a round, oval, elliptical, or rectangular shape. A person skilled in the art will appreciate that while the central spacer 12 is described as being adapted to be positioned between the spinous processes of adjacent vertebrae, that the spinous processes of the adjacent vertebrae do not necessarily need to be present, as they may be removed in a laminectomy procedure. Accordingly, the central spacer 12 can be positioned between other posterior elements of the adjacent vertebrae, or it can be positioned in the general vicinity of the removed spinous processes.

The central spacer 12 can also be formed from a rigid material, or it can be formed from a semi-rigid, pliable or compressible material to allow some compression of the central spacer 12 to occur upon extension of the adjacent vertebrae. A person having ordinary skill in the art will appreciate that the material used to form the central spacer 12 can be selected based on the intended use. For example, a material can be selected based on the patient's size and condition to have a particular stiffness, deformability, or compressibility which corresponds to a desired degree of extension intended. The particular properties of the central spacer 12 can also vary throughout the central spacer 12, and the central spacer 12 can be uniform or non-uniform throughout the body thereof. In an exemplary embodiment, the central spacer 12 is formed from a polymer, and more preferably a biocompatible polymer, such as polyurethane, composite reinforced polyurethane, silicone, etc.

The arms 14a, 14b, 16a, 16b that extend from the central spacer 12 can also have a variety of configurations, shapes, and sizes, and the configuration of each arm 14a, 14b, 16a, 16b can vary depending on the particular procedure being performed and the desired implant location. In general, the arms 14a, 14b, 16a, 16b are preferably rod-shaped members having a substantially elongate shape. While the arms 14a, 14b, 16a, 16b can extend from any portion of the central spacer 12, in the exemplary embodiment shown in FIG. 1A, the superior arms 16a, 16b extend from opposed superior ends of the lateral sides 12a, 12b of the anterior portion 12c of the central spacer 12. The superior arms 16a, 16b can diverge with respect to one another away from the central spacer 12, and each arm 16a, 16b can have a substantially curved configuration. Such a shape allows the superior arms 16a, 16b to mate to the pedicles of a vertebra positioned superior to the device 10. The inferior arms 14b, 16b can also extend from opposed lateral sides 12a, 12b of the central spacer 12, however in the illustrated exemplary embodiment they extend from an inferior end of the anterior portion 12c of the central spacer 12. The inferior arms 14b, 16b can extend laterally such that they are substantially co-axial with one another, or they can extend in an inferior direction with respect to the central spacer 12. The laterally-extending arms 14b, 16b shown in FIG. 1B allow the arms 14b, 16b to mate to the pedicles of a vertebra positioned inferior to the central spacer 12. Again, a person skilled in the art will appreciate that the shape, size, and configuration of the arms 14a, 14b, 16a, 16b can vary depending on the intended use and implant location.

Each arm 14a, 14b, 16a, 16b can also be substantially pliable to control or provide resistance to movement, e.g., flexion, extension, lateral bending, and/or axial rotation, of the adjacent vertebrae coupled thereto. The amount of pliability, e.g., flexibility and/or elasticity, of each arm 14a, 14b, 16a, 16b can vary depending on the properties of the material used to form the device 10, and a material can be selected to achieve a desired result. The pliability can also vary along the length of each arm 14a, 14b, 16a, 16b. For example, the arms 14a, 14b, 16a, 16b can be more pliable adjacent to the central spacer 12, and can be more rigid adjacent to the terminal end thereof. Rigid terminals ends are particularly advantageous to facilitate mating of the device 10 to adjacent vertebrae. Other exemplary techniques for providing rigid terminal ends include, by way of non-limiting example, metal sleeves that slide over the ends of the arms 14a, 14b, 16a, 16b and that can be crimped to engage the arms 14a, 14b, 16a, 16b and prevent the sleeves from sliding off. Alternatively, a metal over-mold or a hard polymer over-mold can be provided on the ends of the arms 14a, 14b, 16a, 16b.

In one exemplary embodiment, the device 10 has a unitary configuration and is formed from an elastomer with multiple durometers, i.e., varying degrees of surface resistivity or material hardness throughout the device 10. For example, the central spacer 12 can have an intermediate durometer, the portion of the arms 14a, 14b, 16a, 16b adjacent to the central spacer 12 can have a low durometer, and the terminal ends of the arms 14a, 14b, 16a, 16b can have a high durometer such that they are extremely rigid for interfacing with fastening elements to mate the arms 14a, 14b, 16a, 16b to adjacent vertebrae.

Figure 1B:
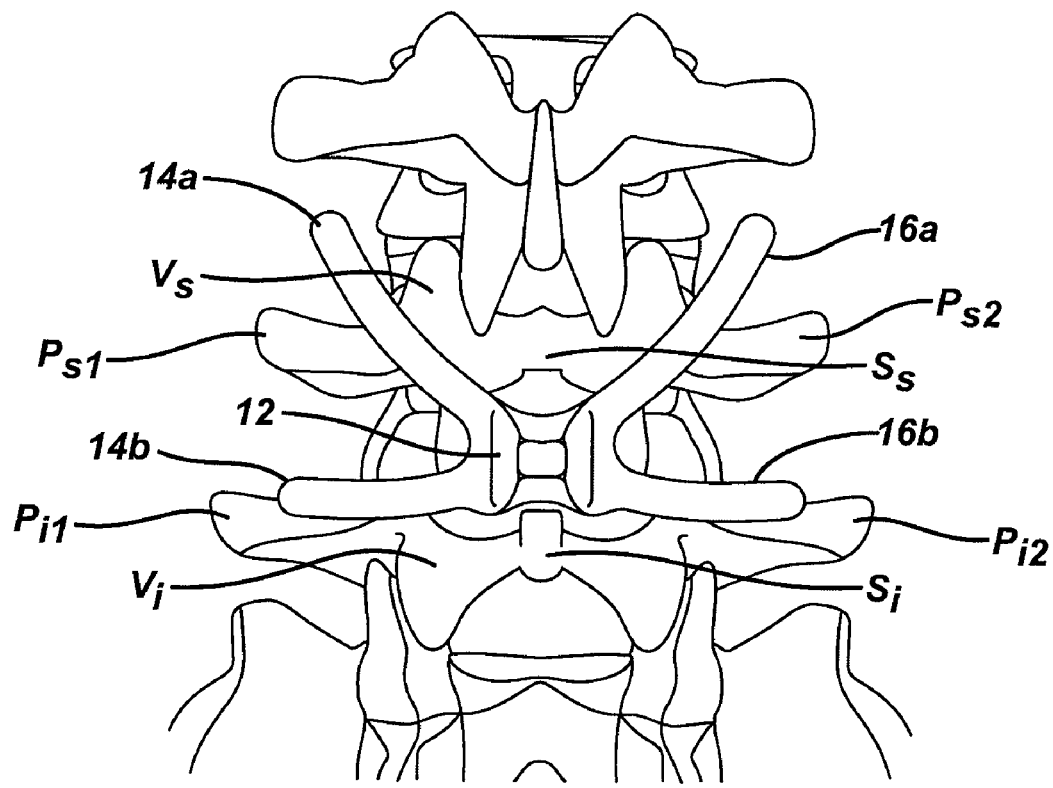
FIG. 1B is a posterior view of a portion of a human spinal column having the device shown in FIG. 1A implanted therein.

FIG. 1B illustrates spinal stabilization device 10 in use. As shown, the central spacer 12 is positioned between two spinous processes $S_s$, $S_i$ of two adjacent vertebrae, i.e., a superior vertebra $V_s$ and an inferior vertebra $V_i$. Where the device 10 is formed from a pliable material, the spacer 12 can be positioned between the spinous processes $S_s$, $S_i$ by squeezing two of the arms, e.g., arms 14a, 14b together and passing the arms 14a, 14b between the spinous processes $S_s$, $S_i$. This will avoid the need to sacrifice the supraspinous ligament that connects the spinous processes $S_s$, $S_i$. Once the spacer 12 is positioned between the spinous processes $S_s$, $S_i$ of the adjacent vertebrae $V_s$, $V_i$, the tension of the ligament can optionally be used to determine whether the spacer 12 has the appropriate size or height. If the spacer 12 is too small or too large, the device 10 can be removed and replaced with another device 10 having an appropriately sized spacer 12.

As is further shown in FIG. 1B, when the central spacer 12 is positioned between the spinous processes $S_s$, $S_i$, the superior arms 14a, 16a extend toward the pedicles $P_{s1}$, $P_{s2}$ of the superior vertebra $V_s$, and the inferior arms 14b, 16b extend toward the pedicles $P_{i1}$, $P_{i2}$ of the inferior vertebra $V_i$. While not shown, one or more bone-engaging devices, such as a mono-axial or poly-axial bone screw can be used to mate the arms 14a, 14b, 16a, 16b to the pedicles $P_{s1}$, $P_{s2}$, $P_{i1}$, $P_{i2}$. Alternatively, a mobile poly-axial screw can be used. Exemplary mobile poly-axial screws are described in U.S. Publication No. 2004/0225289 of Biedermann et al., and WO 2005/044123 of Biedermann et al., which are hereby incorporated by reference in their entirety. The central spacer 12 can at least partially rotate to facilitate mating of the arms 14a, 14b, 16a, 16b to the pedicles $P_{s1}$, $P_{s2}$, $P_{i1}$, $P_{i2}$. While four arms 14a, 14b, 16a, 16b are provided, it is not necessary to mate all four arms 14a, 14b, 16a, 16b to the adjacent vertebrae $V_s$, $V_i$. Only two of the four arms 14a, 14b, 16a, 16b can be mated to the vertebrae $V_s$, $V_i$. One exemplary embodiment of a prior art polyaxial bone screw will be discussed in more detail below with respect to FIG. 14. A person skilled in the art will appreciate that virtually any technique known in the art for mating a rod to bone can be used to implant the various exemplary spinal stabilization devices disclosed herein. Once implanted 10, the central spacer 12 can function to limit or stop extension of the adjacent vertebrae $V_s$, $V_i$, and the arms 14a, 14b, 16a, 16b can control or provide resistance to movement, e.g., flexion, extension, lateral bending, and/or axial rotation of the adjacent vertebrae $V_s$, $V_i$. The device 10 can also be effective to provide stability to the facet joints, which may or may not be removed, and to other posterior elements, such as the natural disc, a nucleus replacement, or a disc replacement. The device 10 is particularly advantageous for use with nucleus replacements, as the device 10 can offload the nucleus replacement during axial rotation of the adjacent vertebrae.

Figure 2:
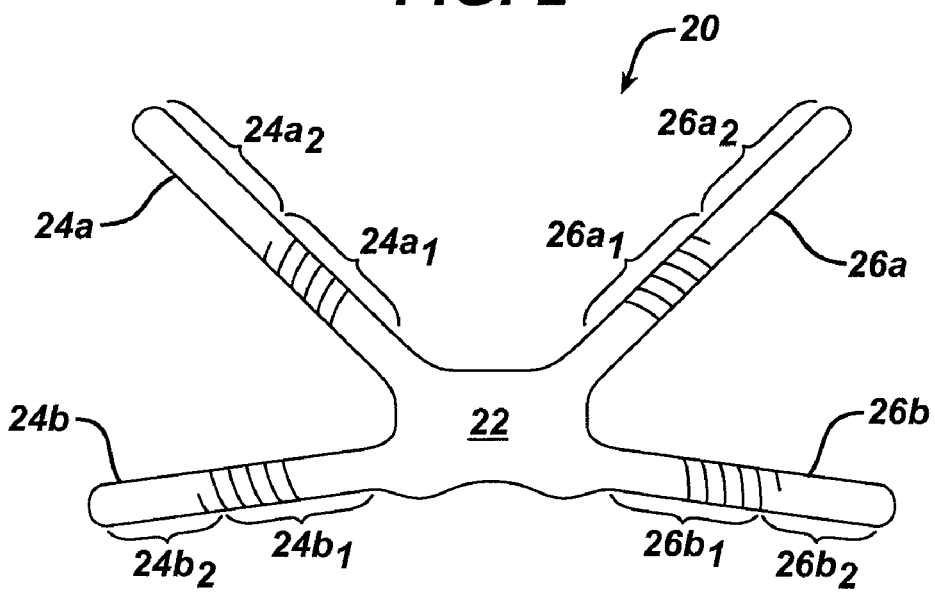
FIG. 2 is a posterior view of another exemplary embodiment of a spinal stabilization device having a central spacer with pliable arms coupled thereto.

FIG. 2 illustrates another exemplary embodiment of a spinal stabilization device 20. The device 20 is very similar to device 10 shown in FIGS. 1A and 1B, however device 20 is not of a unitary construction, but rather the arms 24a, 24b, 26a, 26b are fixedly mated to the central spacer 22. The arms 24a, 24b, 26a, 26b can be mated to the central spacer 22 using a variety of techniques, however in the embodiment shown in FIG. 2 the central spacer 22 is formed from a polymeric material and the arms 24a, 24b, 26a, 26b are adhered thereto using an adhesive or an overmold. The arms 24a, 24b, 26a, 26b also include a pliable region formed thereon to provide pliability, e.g., flexibility and/or elasticity, to a portion of the arms 24a, 24b, 26a, 26b. In particular, each arm 24a, 24b, 26a, 26b is in the form of a spring rod having a coiled region 24c, 24d, 26c, 26d formed thereon, preferably on a first portion $24a_1$, $24b_1$, $26a_1$, $26b_1$ of each arm 24a, 24b, 26a, 26b. The coiled region 24c, 24d, 26c, 26d can be formed from a coiled cut-out formed in the arms 24a, 42b, 26a, 26b to allow the arms 24a, 24b, 26a, 26b to flex. By providing the coiled region 24c, 24d, 26c, 26d in the first portion $24a_1$, $24b_1$, $26a_1$, $26b_1$ of each arm 24a, 24b, 26a, 26b, a second or terminal portion $24a_2$, $24b_2$, $26a_2$, $26b_2$ of each arm 24a, 24b, 26a, 26b can be substantially rigid to facilitate mating of the device 20 to bone. A person skilled in the art will appreciate that the arms 24a, 24b, 26a, 26b can be formed from a variety of materials, but in one exemplary embodiment the arms 24a, 24b, 26a, 26b are formed from a metal, such as a titanium alloy, stainless steel, or a shape-memory material.

Figure 3:
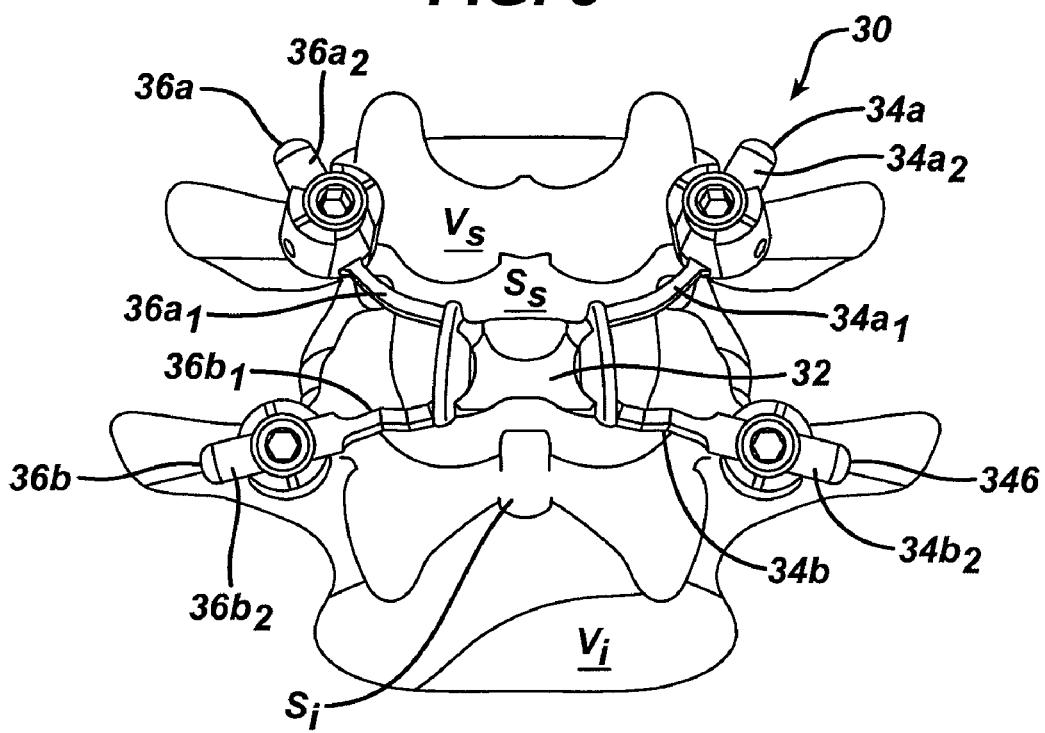
FIG. 3 is a posterior view of a portion of a human spinal column showing a spinal stabilization device implanted therein and having a central spacer with a first pair of arms coupled to a first lateral side thereof and a second pair of arms coupled to a second, opposed lateral side thereof in accordance with another exemplary embodiment.

While FIGS. 1A-2 illustrate various embodiments of spinal stabilization devices 10, 20 that have arms integrally formed with or fixedly mated to the central spacer, the arms can optionally be removably matable to the central spacer. Removable arms can be advantageous as they will allow the spacer to be positioned between the spinous processes or other posterior elements without sacrificing the ligament. The arms can then be attached to the central spacer and mated to the bone to stabilize the vertebrae. While various techniques can be used to provide removable arms, FIG. 3 illustrates one exemplary embodiment of a spinal stabilization device 30 having removable arms. As shown, the device includes a central spacer 32, a first pair of arms 34a, 34b coupled to a first lateral side 32a of the central spacer 32, and a second pair of arms 36a, 36b coupled to a second, opposed lateral side 32b of the central spacer 32. The first pair of arms 34a, 34b can be coupled to or integrally formed with one another, and the second pair of arms 36a, 36b can likewise be coupled to or integrally formed with one another, as shown. The first pair of arms 34a, 34b can removably mate to the first lateral side 32a of the central spacer 32 and the second pair of arms 36a, 36b can removably mate to the second lateral side 32b of the central spacer 32, or alternatively the first and second pair of arms 34a, 34b, 36a, 36b can mate to one another through a bore formed in the central spacer 32. A fastening element such as a set screw, pin, locking nut, rivet, etc., can be used to mate the arms 34a, 34b, 36a, 36b to the central spacer 32 and/or one another. A person skilled in the art will appreciate that virtually any fastening mechanism can be used to mate the pairs of arms 34a, 34b, 36a, 36b to the central spacer 32.

Each arm 34a, 34b, 36a, 36b can also be pliable to control or provide resistance to movement, e.g., flexion, extension, lateral bending, and/or axial rotation of the adjacent vertebrae coupled thereto. While various techniques can be used to provide pliability, including those previously discussed herein, in one exemplary embodiment each arm $34a$, $34b$, $36a$, $36b$ can include a first portion $34a_1$, $34b_1$, $36a_1$, $36b_1$ adjacent to the central spacer 32 that is formed form a thin pliable material, and a second or terminal portion $34a_2$, $34b_2$, $36a_2$, $36b_2$ that is formed from a more rigid material to allow the arms $34a$, $34b$, $36a$, $36b$ to be mated to bone.

In use, the configuration shown in FIG. 3 allows the central spacer 32 to be positioned prior to attaching the arms $34a$, $34b$, $36a$, $36b$ thereto, thereby allowing the ligament extending between the spinous processes $S_s$, $S_i$ of the adjacent vertebrae $V_s$, $V_i$ to maintain in tact. The configuration can also allow the arms $34a$, $34b$, $36a$, $36b$ to rotate relative to the central spacer 32 prior to locking the arms $34a$, $34b$, $36a$, $36b$ thereto, thus allowing the arms $34a$, $34b$, $36a$, $36b$ to be positioned at desired. Furthermore, although not shown in detail, the attachment to the central spacer 32 can be done using hemispherical mating surfaces to allow pivotal adjustment of the arms $34a$, $34b$, $36a$, $36b$ relative to the spacer 32. Such an adjustment mechanism allows accurate placement of the spacer 32 for a variety of anatomies without putting excessive loading on the arms $34a$, $34b$, $36a$, $36b$. After locating the spacer 32 and the arms $34a$, $34b$, $36a$, $36b$, all units can be combined using any of a variety of locking mechanisms, including screws, rivets, pins, adhesives, etc.

Figure 4:
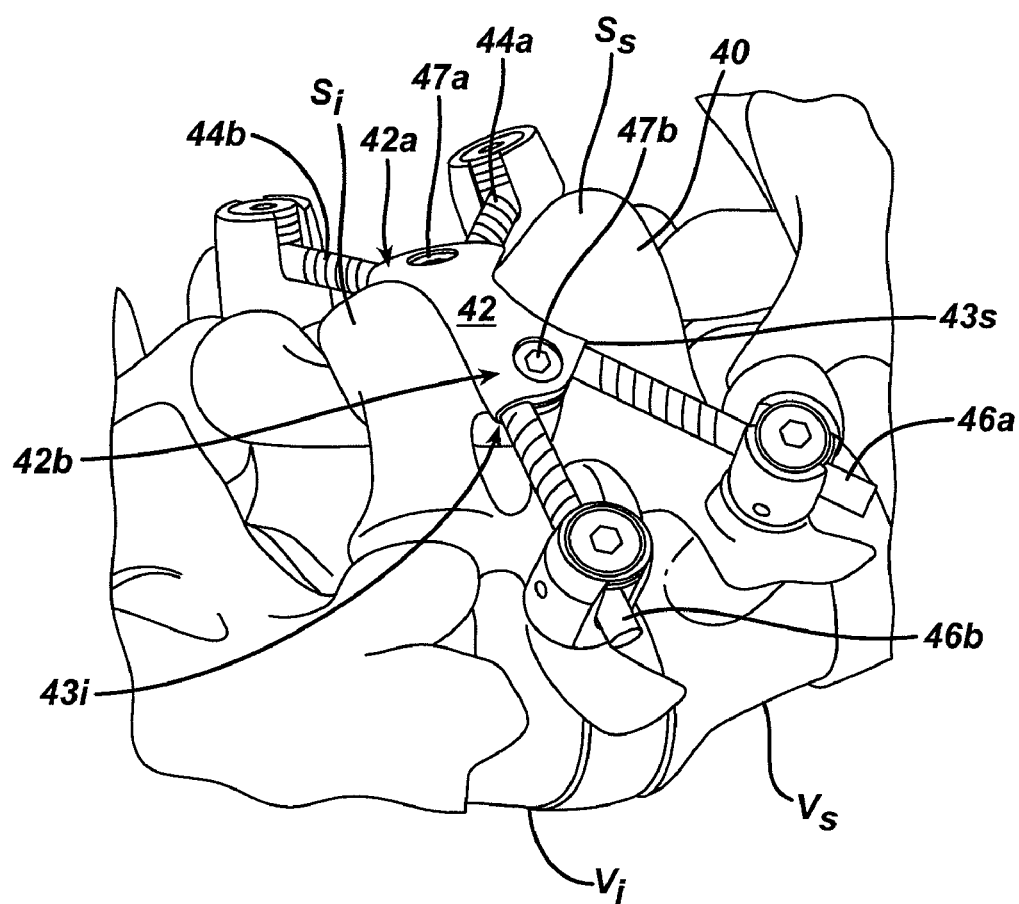
FIG. 4 is a posterior perspective view of a portion of a human spinal column having an exemplary embodiment of a spinal stabilization device implanted therein and having a central spacer with removable arms coupled thereto.

FIG. 4 illustrates another exemplary embodiment of a spinal stabilization device 40 having removable arms $44a$, $44b$, $46a$, $46b$. As shown, the device 40 includes a central spacer 42 that is adapted to be positioned between spinous processes $S_s$, $S_i$ of adjacent superior and inferior vertebra $V_s$, $V_i$, and four arms $44a$, $44b$, $46a$, $46b$ that are removably mated to the central spacer 42. The arms $44a$, $44b$, $46a$, $46b$ can have a variety of configurations, but in the illustrated embodiment they are very similar to the spring rod arms $24a$, $24b$, $26a$, $26b$ of the device 20 shown in FIG. 2. Accordingly, the arms $44a$, $44b$, $46a$, $46b$ will not be described in detail.

The central spacer 42 can have virtually any shape and size, but in the illustrated embodiment it has a generally elongate shape with a height at a mid-portion that is less than a height of the central spacer 42 at the opposed lateral sides thereof. Each lateral side $42a$, $42b$ can be in the form of a clamp to receive the arms $44a$, $44b$, $46a$, $46b$ therein. For example, the lateral sides $42a$, $42b$ can include a superior opening and an inferior opening formed therein. FIG. 4 only illustrates the superior and inferior openings $43_s$, $43_i$ in lateral side $42b$. Each opening $43_s$, $43_i$ has a shape and size that allows one end of one of the arms $44a$, $44b$, $46a$, $46b$ to be slid therein. A locking mechanism can then be used to cause the central spacer 42 to clamp down onto and engage the arms $44a$, $44b$, $46a$, $46b$. While the locking mechanism can have a variety of configurations, in the illustrated embodiment the locking mechanisms are in the form of set screws $47a$, $47b$ that extend through threaded bores formed in the posterior and anterior faces of the central spacer 42 to pull the posterior and anterior faces toward one another, thereby causing the central spacer 42 to engage the arms $44a$, $44b$, $46a$, $46b$.

In use, the central spacer 42 is preferably passed between the spinous processes $S_s$, $S_i$ of the adjacent vertebrae $V_s$, $V_i$, and the arms $44a$, $44b$, $46a$, $46b$ can then be slid into the corresponding openings in the central spacer 42. The locking mechanisms $47a$, $47b$ can be pre-disposed within the central spacer 42, or they can be inserted into the central spacer 42 after the arms $44a$, $44b$, $46a$, $46b$ are disposed therein. The locking mechanisms $47a$, $47b$ can be tightened to engage the arms $44a$, $44b$, $46a$, $46b$, preventing removably thereof from the central spacer 42. At least two of the arms, and preferably are four of the arms $44a$, $44b$, $46a$, $46b$, can then be mated to the superior and inferior vertebrae $V_s$, $V_i$ to provide stability to the posterior elements of the spine. In this embodiment, the central spacer 42 is preferably formed from a rigid material, such as a metal, and thus the central spacer 42 can function as a hard stop to prevent extension of the vertebrae $V_s$, $V_i$. The spring rod arms $44a$, $44b$, $46a$, $46b$ will control or provide resistance to movement, e.g., flexion, extension, lateral bending, and/or axial rotation, of the vertebrae $V_s$, $V_i$. A person skilled in the art will appreciate that a variety of other techniques can be used to provide arms that removably mate to a central spacer.

Figure 5:
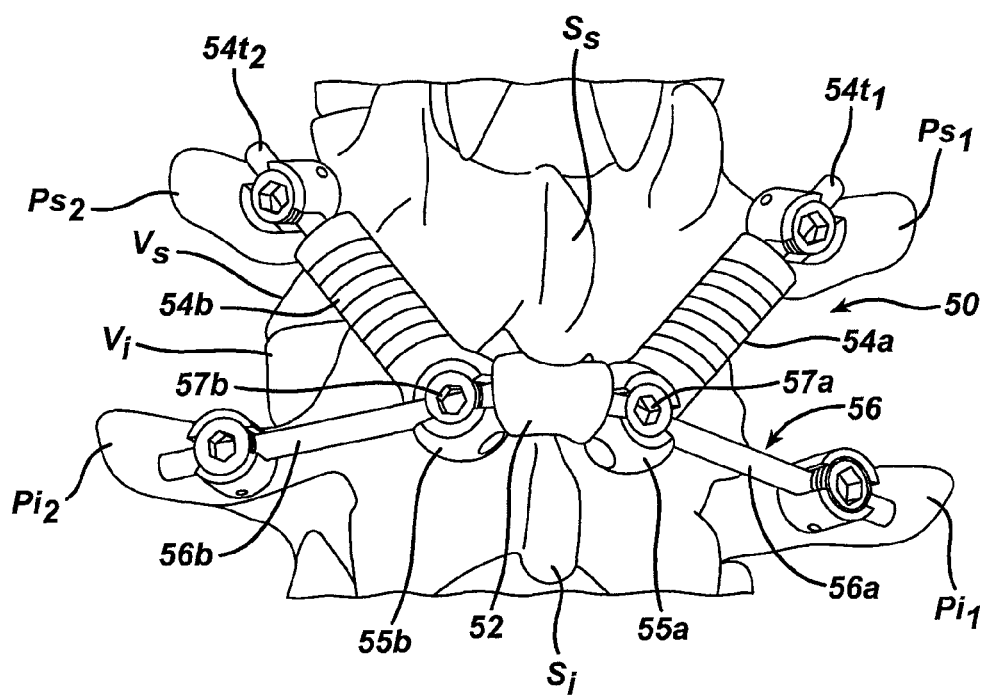
FIG. 5 is a posterior view of a portion of a human spinal column having another exemplary embodiment of a spinal stabilization device implanted therein and having a central spacer with an arm slidably disposed therethrough to form opposed first and second arms, and third and fourth arms coupled to the first and second arms.

FIG. 5 illustrates another exemplary embodiment of a spinal stabilization device 50. In this embodiment, the device 50 includes a central spacer 52 with an elongate arm 56 that is slidably disposed through a laterally-extending lumen formed in the central spacer 52. As a result, the elongate arm 56 forms opposed first and second arms $56a$, $56b$ extending from opposed lateral sides of the central spacer 52. The device 50 also include a third arm $54a$ that is removably attached to the first arm $56a$, and a fourth arm $54b$ that is removably attached to the second arm $56b$. Such a configuration will allow the central spacer 52 with arm 56 disposed therethrough to be inserted between the spinous processes $S_s$, $S_i$ of adjacent superior and inferior vertebrae $V_s$, $V_i$, and then the third and fourth arms $54a$, $54b$ can be mated thereto.

The central spacer 52 and the elongate arm 56 can have a variety of configurations, but as shown the central spacer 52 is substantially tubular in shape and the elongate arm 56 is in the form of an elongate rod that extends through the central spacer 52. The elongate arm 56 can be curved to facilitate mating thereof to the pedicles $P_{i2}$, $P_{i2}$ of the inferior vertebra $V_i$, as shown, or they can have a shape to facilitate mating thereof to the pedicles $P_{s1}$, $P_{s2}$ of the superior vertebra $V_s$.

The third and fourth removable arms $54a$, $54b$ can also have a variety of configurations, but in the illustrated exemplary embodiment they are coiled to provide pliability, and they are adapted to mate to the first and second arms $56a$, $56b$. In particular, the third and fourth arms $54a$, $54b$ each include a spherical head $55a$, $55b$ formed on one end thereof for seating a portion of the elongate arm 56 therein. The spherical head $55a$, $55b$ is adapted to receive a locking mechanism such as a set screw $57a$, $57b$, therein for locking the third and fourth arms $54a$, $54b$ to the first and second arms $56a$, $56b$. The third and fourth arms $54a$, $54b$ can also include a hollow coiled portion extending from the spherical head $55a$, $55b$ for providing pliability to the arms $54a$, $54b$ to allow flexion of the adjacent vertebrae $V_s$, $V_i$. The third and fourth arms $54a$, $54b$ can, however, have a variety of other configurations and they can be formed from a pliable and/or rigid material. As is further shown in FIG. 5, a terminal end $54_{t1}$, $54_{t2}$ of the third and fourth arms $54a$, $54b$ can be in the form of rods that are adapted to be received within a bone-engaging device, such as a polyaxial bone screw as will be discussed in more detail below. A person skilled in the art will appreciate that a variety of other techniques can be used to removably mate one or more arms to the elongate arm 56.

In use, as indicated above, the central spacer 52, with or without the elongate arm 56 disposed therethrough, is preferably positioned between the spinous processes $S_s$, $S_i$. In an exemplary embodiment, the elongate arm 56 is preferably pre-disposed within the central spacer 52, and the central spacer 52 is configured to provide a snug fit with the elongate arm 56 to prevent sliding of the arm 56 with respect to the spacer 52. Once the spacer 52 and arm 56 are properly positioned, the third and fourth arms $54a$, $54b$ can be coupled to the first and second arms 56a, 56b. Preferably at least two of the arms 54a, 54b, 56a, 56b are also coupled to the pedicles $P_{s1}$, $P_{s2}$, $P_{i1}$, $P_{i2}$ of the vertebrae $V_s$, $V_i$.

In other embodiments, the spinal stabilization device can have a central spacer that is adjustably matable to opposed arms to allow the central spacer to be positioned as desired. FIG. 6A illustrates one such exemplary embodiment. As shown, the spinal stabilization device 60 generally includes a central spacer 62 with a cross-connector 68 coupled thereto, and opposed arms 64, 66 that are matable to the cross-connector 68. In particular, the central spacer 62, which can have any shape including square, cylindrical, or rectangular, has a central lumen formed therein and extending between opposed lateral sides thereof. The cross-connector 68 can be in the form of a clamp that is adapted to extend through the central lumen formed in the central spacer 62. As shown in detail in FIG. 6C, the cross-connector 68 includes two members 69a, 69b that define two openings $68o_1$, $68o_2$ formed therebetween for receiving the arms 64, 66 of the device 60. A fastening element, such as a set screw 68s, can be inserted through a central bore 68c formed in the cross-connector 68 to engage the arms 64, 66 within the openings $68o_1$, $68o_2$. A person skilled in the art will appreciate that the cross-connector 68 can have a variety of other configurations, and that a variety of other techniques can be used to mate the arms 64, 66 to the central spacer 62. By way of non-limiting example, FIG. 6D illustrates another embodiment of a cross-connector 68' for use with the device 60 shown in FIG. 6A. In this embodiment, the cross-connector 68' has hook-shaped ends 68a', 68b', rather than openings formed therethrough, for seating the arms 64, 66 of the device 60. A locking mechanism 68s' can be inserted through a central bore 68c' to cause opposed engagement mechanisms 69a', 69b' to slide outward and engage the arms 64, 66.

The arms 64, 66 of the device 60 can also have a variety of configurations, but in an exemplary embodiment they are substantially similar to the arms 34a, 34b, 36a, 36b shown in FIG. 3. In this embodiment, however, each arm 64, 66 is substantially planar except for superior and inferior terminal end portions 64a, 64b, 66a, 66b and a central portion 64c, 66c of each arm 64, 66. The superior and inferior terminal end portions 64a, 64b, 66a, 66b and the central portion 64c, 66c can have a substantially cylindrical shape to allow the arms 64, 66 to mate to adjacent vertebrae, and to allow the central portions 64c, 66c to fit within the opening $68o_1$, $68o_2$ in the cross-connector 68. A person skilled in the art will appreciate that each arm 64, 66 can be cylindrical along the entire length thereof, or that the arms 64, 66 can have a variety of other shapes.

In use, when the arms 64, 66 are mated to adjacent superior and inferior vertebrae $V_s$, $V_i$, as shown in FIG. 6A, the central spacer 62 and cross-connector 68 can be moved proximally and distally, as well as in an anterior and posterior direction, relative to the adjacent vertebrae $V_s$, $V_i$ to position the central spacer 62 as desired. The angle of the arms 64, 66 relative to the adjacent vertebrae $V_s$, $V_i$ can also be adjusted using polyaxial bone screws, mobile bone screws, or screws that lock, to connect the arms to the adjacent vertebrae $V_s$, $V_i$, as will be discussed in more detail with respect to FIG. 9. Once the central spacer 62 and the cross-connector 68 are in a desired position, a locking mechanism, such as a set screw 68s, can be inserted through a central bore formed in the central spacer 62 and through the central bore 68c formed in the cross-connector 68 to cause the cross-connector 68 to clamp onto and engage the arms 64, 66. As a result, the central spacer 62 can be maintained in a substantially fixed position relative to the arms 64, 66. A person skilled in the art will appreciate that the arms 64, 66, the central spacer 62, and the cross-connector 68 can have a variety of other configurations, including various other configurations disclosed herein. The arms 64, 66, the central spacer 62, and the cross-connector 68 can also be formed from a variety of materials, including polymeric materials, metallic materials, and combinations thereof, and the materials can be pliable or rigid, or combinations thereof.

Figure 7:
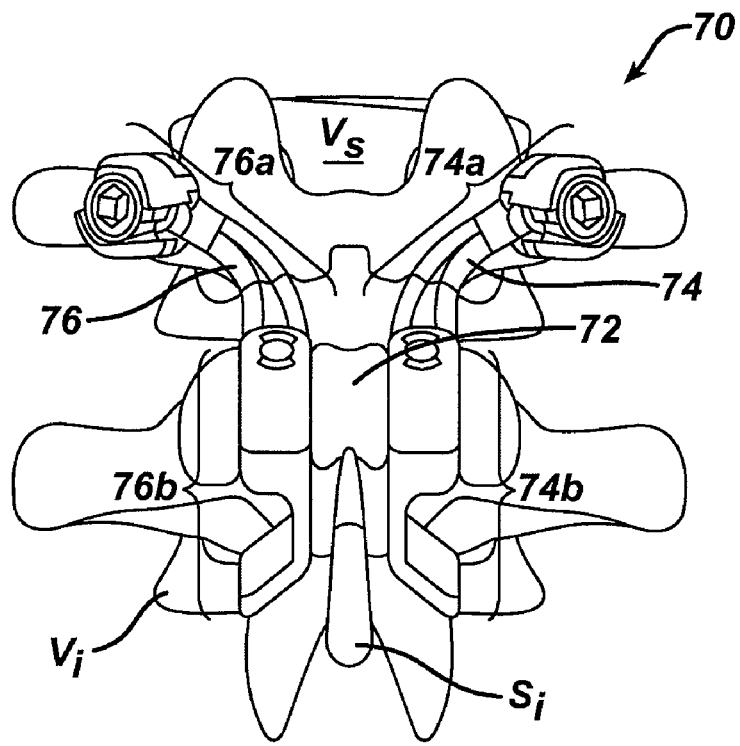
FIG. 7 is a posterior view of yet another exemplary embodiment of a spinal stabilization device having opposed arms that are adapted to engage a spinous process.

In other exemplary embodiments, the spinal stabilization device can be adapted to engage at least one spinous process to control or provide resistance to movement, e.g., flexion, extension, lateral bending, and/or axial rotation, of adjacent vertebrae. FIG. 7 illustrates one exemplary embodiment of such a spinal stabilization device 70. As shown, the device 70 is substantially Y-shaped and includes a central spacer 72 with a first arm 74 coupled to a first lateral side thereof, and a second arm 76 coupled to a second lateral side thereof. The arms 74, 76 can be fixedly mated to, removably mated to, or of unitary construction with the central spacer 72. For example, each arm 74, 76 can be adapted to receive a fastening element, such as a set screw, therethrough for mating each arm 74, 76 to the central spacer 72. Each arm 74, 76 can also include a first portion, e.g., a superior portion 74a, 76a that is adapted to mate to a superior vertebra $V_s$, and a second portion, e.g., an inferior portion 74b, 76b that is adapted to be positioned adjacent to the spinous process $S_i$ of an inferior vertebra $V_i$. The first portion 74a, 76a of each arm 74, 76 can have a variety of shapes and sizes to facilitate mating to the superior vertebra $V_s$, but in the illustrated exemplary embodiment the superior portion 74a, 76a of each arm 74, 76 is substantially curved such that the arms 74, 76 diverge with respect to one another away from the central spacer 72. The arms 74, 76 can also be formed from a variety of materials, including pliable materials to allow the arms to be positioned as desired during implantation. Where the device 70 only attaches to the vertebrae by the arms 74, 76, the arms can optionally be rigid, as the inferior portion 74b, 76b of the arms 74, 76 will allow controlled movement of the adjacent vertebrae.

The inferior portion 74b, 76b of each arm 74, 76 can also have a variety of shapes and sizes, but in an exemplary embodiment the inferior portions 74b, 76b are adapted to engage the inferior spinous process $Si$ therebetween, preferably at the base thereof, to substantially control or provide resistance to movement, e.g., flexion, extension, lateral bending, and/or axial rotation, of the adjacent vertebrae $V_s$, $V_i$. By way of non-limiting example, the inferior portions 74b, 76b can be substantially elongate, flat members that grip the spinous process $S_i$, or they can be rod-shaped and can include protective covers disposed there over or features formed thereon to facilitate gripping of the spinous process $S_i$. The inferior portions 74b, 76b can also be pliable to provide some resistance to flexion, extension, lateral bending, and/or axial rotation. The inferior portions 74b, 76b can also be adapted to contact the lamina of the inferior vertebra $V_i$ to further aid in limiting extension, axial rotation, and/or lateral bending of the adjacent vertebrae. For example, the distal-most or terminal end of the inferior portions 74b, 76b can each have a shape, e.g., flat, rounded, spherical, etc., that is adapted to abut against the lamina of the inferior vertebra $V_i$, and the shape and size can be configured to maximize the contact area between the inferior portions 74b, 76b and the inferior vertebra $V_i$.

Figure 8:
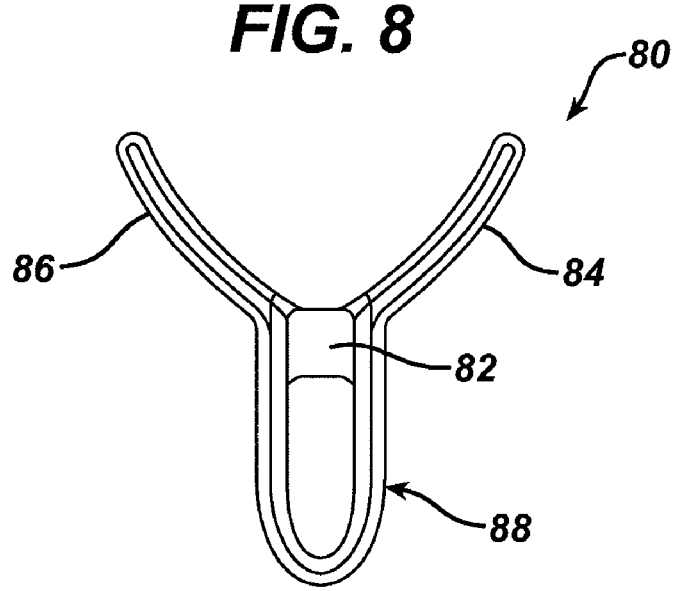
FIG. 8 is a posterior view of another exemplary embodiment of a substantially U-shaped spinal stabilization device having a U-shaped member that is adapted to engage a spinous process.

In another embodiment, the stabilization device can engage the spinous process to further control or provide resistance to movement of the adjacent vertebrae. FIG. 8 illustrates one exemplary embodiment of such a stabilization device 80. As shown, the device 80 is similar to device 70, except that the inferior portions of the arms 84, 86 are coupled to one another to form a U-shaped member 88. The U-shaped member 88 can have a variety of configurations and it can be integrally formed with the device 80, or it can be separate from the device 80 to allow it to be coupled to the device 80 either prior to or after implantation. Where the device 80 has a multi-component configuration, by way of non-limiting example the U-shaped member 88 can be formed from a band or cord that can function as an artificial ligament. Such a configuration allows the U-shaped member 88 to be attached to the device 80 after implantation thereby avoiding the need to cut the supraspinous ligament. In particular, the U-shaped member 88 can be inserted between the interspinous space without disrupting the ligament, and it can then be attached to the device 80.

In use, the central spacer 82 is positioned between adjacent spinous processes, the opposed superior arms 84, 86 are mated to a superior vertebra, and the U-shaped member 88 is positioned around the spinous process to engage the spinous process and thereby control or provide resistance to axial rotation, lateral bending, flexion, and/or extension. For example, during flexion the spinous processes of the adjacent vertebrae will move away from one another. As a result, the U-shaped member 88 will stretch thereby providing resistance to flexion.

A person skilled in the art will appreciate that devices 70 and 80, while shown being adapted to engage a spinous process of an inferior vertebra, can be reversed such that the arms 74, 76, 84, 86 mate to an inferior vertebra, and the device 70, 80 engages a spinous process of a superior vertebra. A person skilled in the art will also appreciate that the devices 70, 80 shown in FIGS. 7 and 8, as well as the various other exemplary spinal fixation devices disclosed herein, can be formed from unitary components, or components that are fixedly or removably mated to the central spacer. The various devices can also include any combination of features disclosed herein and a variety of other features known in the art.

Figure 9:
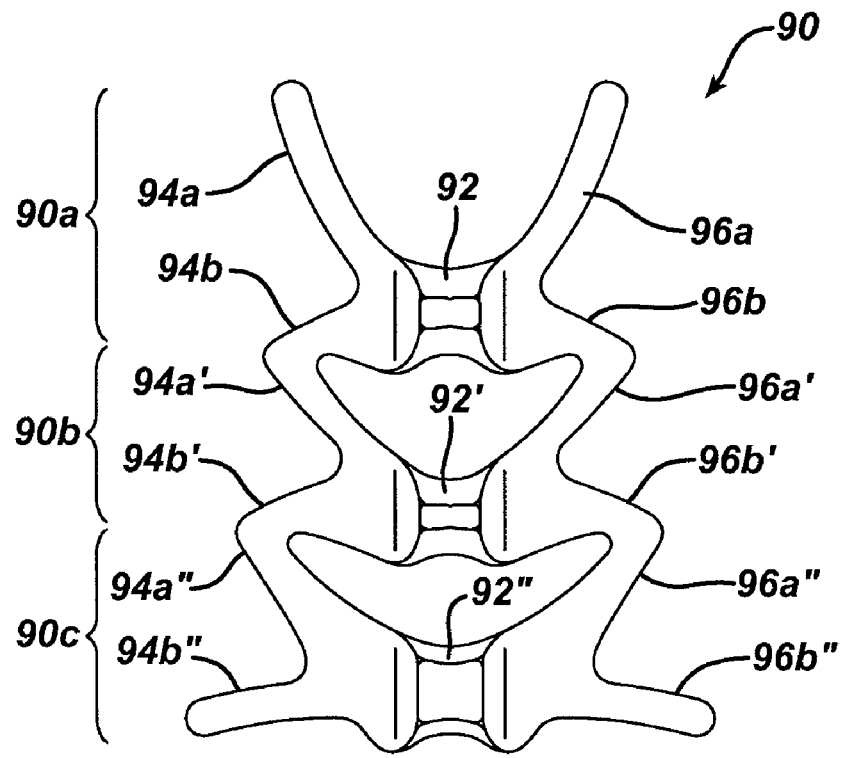
FIG. 9 is a posterior view of yet another exemplary embodiment of a multi-level spinal stabilization device.

Various exemplary multi-level spinal stabilization devices are also provided. FIG. 9 illustrates one exemplary embodiment of a multi-level spinal stabilization device 30. In this embodiment, the device 90 is very similar to device 10 shown in FIGS. 1A and 1B. In particular, the device 90 is formed from three x-shaped bodies 90*a*, 90*b*, 90*c*, each similar to device 10, that are mated to one another. Each body 90*a*, 90*b*, 90*c* has a central spacer 92, 92', 92" with a pair of superior arms 94*a*, 96*a*, 94*a'*, 96*a'*, 94*a"*, 96*a"*, and a pair of inferior arms 94*b*, 96*b*, 94*b'*, 96*b'*, 94*b"*, 96*b"*. The inferior arms 94*b*, 96*b* of the first body 90*a* are mated to the superior arms 94*a'*, 96*a'* of the second body 90*b*, and the inferior arms 94*b'*, 96*b'* of the second body 90*b* are mated to the superior arms 94*a"*, 96*a"* of the third body 90*c*. The arms of the bodies 90*a*, 90*b*, 90*c* can be mated to each other using a variety of techniques, and they can be fixedly mated, removably mated, or unitarily or integrally formed with one another. In the embodiment shown in FIG. 9, the device 90 is formed of a unitary construction, such that the entire device 90 is molded to create a composite device. In use, the device 90 can be implanted by positioning the central spacer 92, 92', 92" of each body 90*a*, 90*b*, 90*c* between spinous processes or other posterior elements of adjacent vertebrae, and connecting the superior arms 94*a*, 94*b* of the first body 90*a* to the superior-most vertebra, and attaching the inferior arms 94*b"*, 96*b"* of the third body 90*b* to the inferior-most vertebra being stabilized. The device 90 can thus function as previously described with respect to FIG. 1A to substantially control or provide resistance to movement, e.g., flexion, extension, lateral bending, and/or axial rotation. The degree to which extension, flexion, lateral bending, and/or axial rotation are controlled can, of course, vary depending on the particular configuration and properties of the device. For example, the material(s) used to form the device 90 can be selected to obtain a desired result. A person having ordinary skill in the art will appreciate that, while only three bodies 90*a*, 90*b*, 90*c* are shown, the device 90 can include any number of bodies based on the desired level of vertebrae being stabilized.

Figure 10:
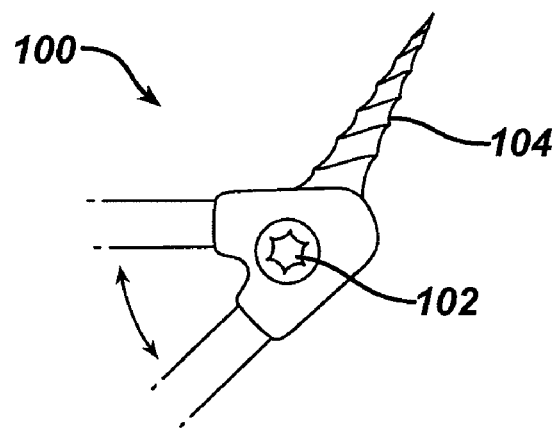
FIG. 10 is a top view of another exemplary of a connector for mating a stabilization device to bone, showing the connector engaging two arms of a spinal stabilization device.

A multi-level spinal stabilization device can also be provided by mating the arms of one spinal stabilization device to the arms of another spinal stabilization device. While various techniques can be used to mate the arms, in one exemplary embodiment a connector can be used. FIG. 10 illustrates one embodiment of a connector 100 that is in the form of a clamp. The illustrated clamp connector 100 is substantially V-shaped or triangular, and it can include two openings (not shown) formed therein for receiving the terminal ends of two arms. A fastening element, such as a set screw 102, can extend through the connector 100 to clamp down on and engage the arms within the connector 100. The connector 100 can also include a bone screw 104 mated thereto to allow the connector 100 to be mated to bone. The bone screw 104 can optionally be polyaxial relative to the connector 100. In other exemplary embodiments, the connector 100 can be modular to allow the two arms mated thereto to be angular adjusted relative to one another. A person skilled in the art will appreciate that a variety of other techniques can be used to mate the arms to one another.

Figure 11A:
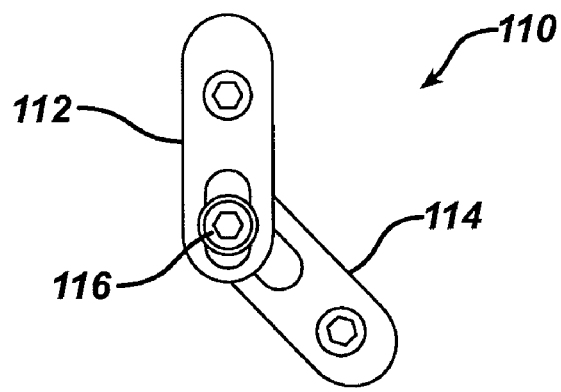
FIG. 11A is a top view of a connector for mating two spinal stabilization devices to one another in accordance with another exemplary embodiment.
Figure 11B:
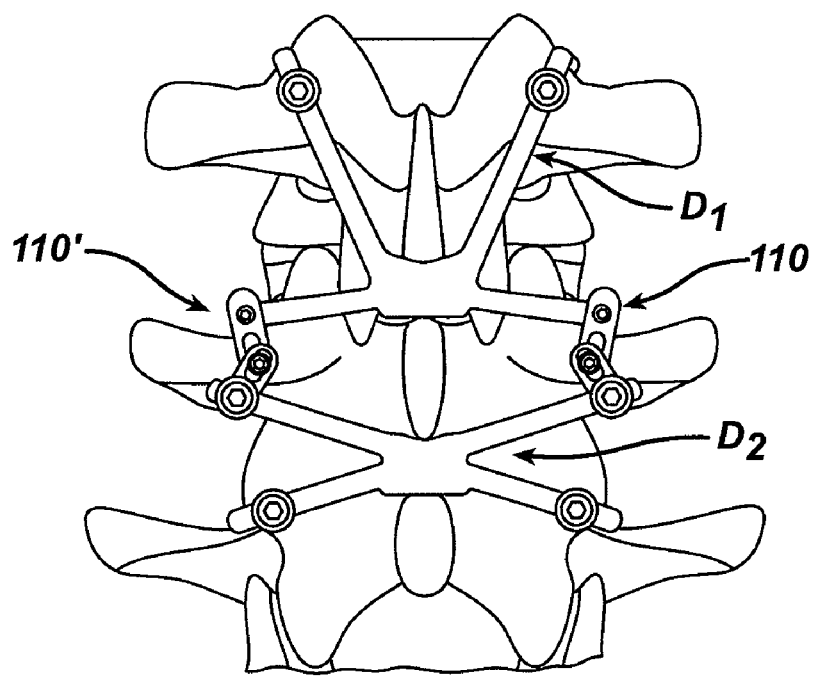
FIG. 11B is a posterior view of a portion of a human spinal column showing two stabilization devices implanted therein and connected to each other with connectors as shown in FIG. 11A.

FIG. 11A illustrated another exemplary embodiment of a connector 110 for mating the arms of two spinal stabilization devices. In this embodiment the connector 110 includes two plate-like members 112, 114 that are pivotally mated to one another using, for example, a fastening element 116, such as a bolt and nut. The terminal end of each plate 112, 114 can be adapted to engage an arm of a spinal stabilization device. This can be achieved using a variety of techniques including, for example, a clamping mechanism, a polyaxial connection, etc., exemplary embodiments of which will be described below with respect to FIGS. 12 and 13. FIG. 11B illustrates connector 110 in use, showing two spinal stabilization devices $D_1$, $D_2$ having arms connected by two connectors 110, 110'.

Figure 12:
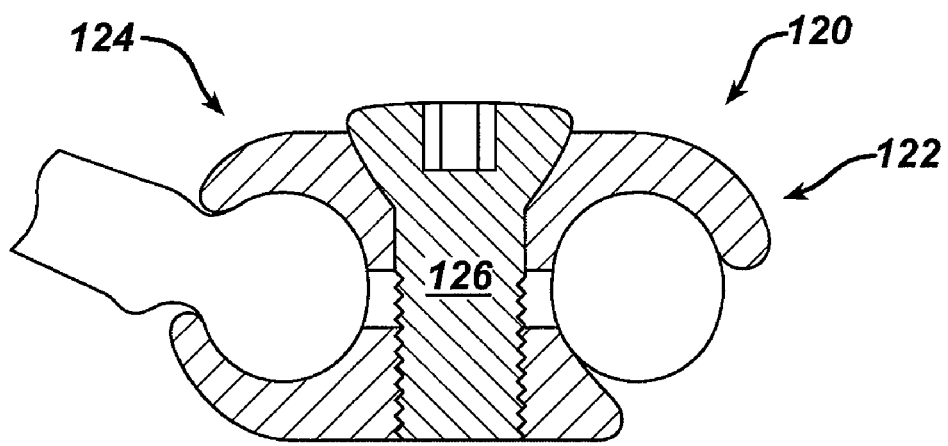
FIG. 12 is a side cross-sectional view of another exemplary embodiment of a connector for mating two spinal stabilization devices to one another.
Figure 13:
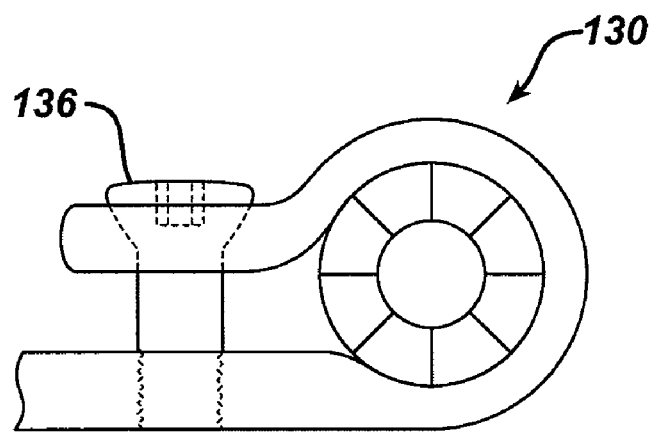
FIG. 13 is a side cross-sectional view of yet another exemplary embodiment of a connector for mating two spinal stabilization devices to one another.

FIGS. 12 and 13 illustrate exemplary embodiments of techniques for connecting the terminal end of each plate 112, 114 to an arm of a spinal stabilization device. In the embodiment shown in FIG. 12, the connector 120 is a clamp having a first end 122 that is adapted to clamp and engage an arm of a stabilization device, and a second end 124 that is adapted to receive a spherical member. The spherical member can be formed on the plate-like member 112, 114 shown in FIGS. 11A and 11B. A single fastening element 126 can be used to close the clamp connector 120. In the embodiment shown in FIG. 13, the connector 130 is similarly in the form of a clamp having a fastening element 136 that is adapted to be disposed therethrough to clamp onto an arm of a spinal stabilization device.

Figure 14:
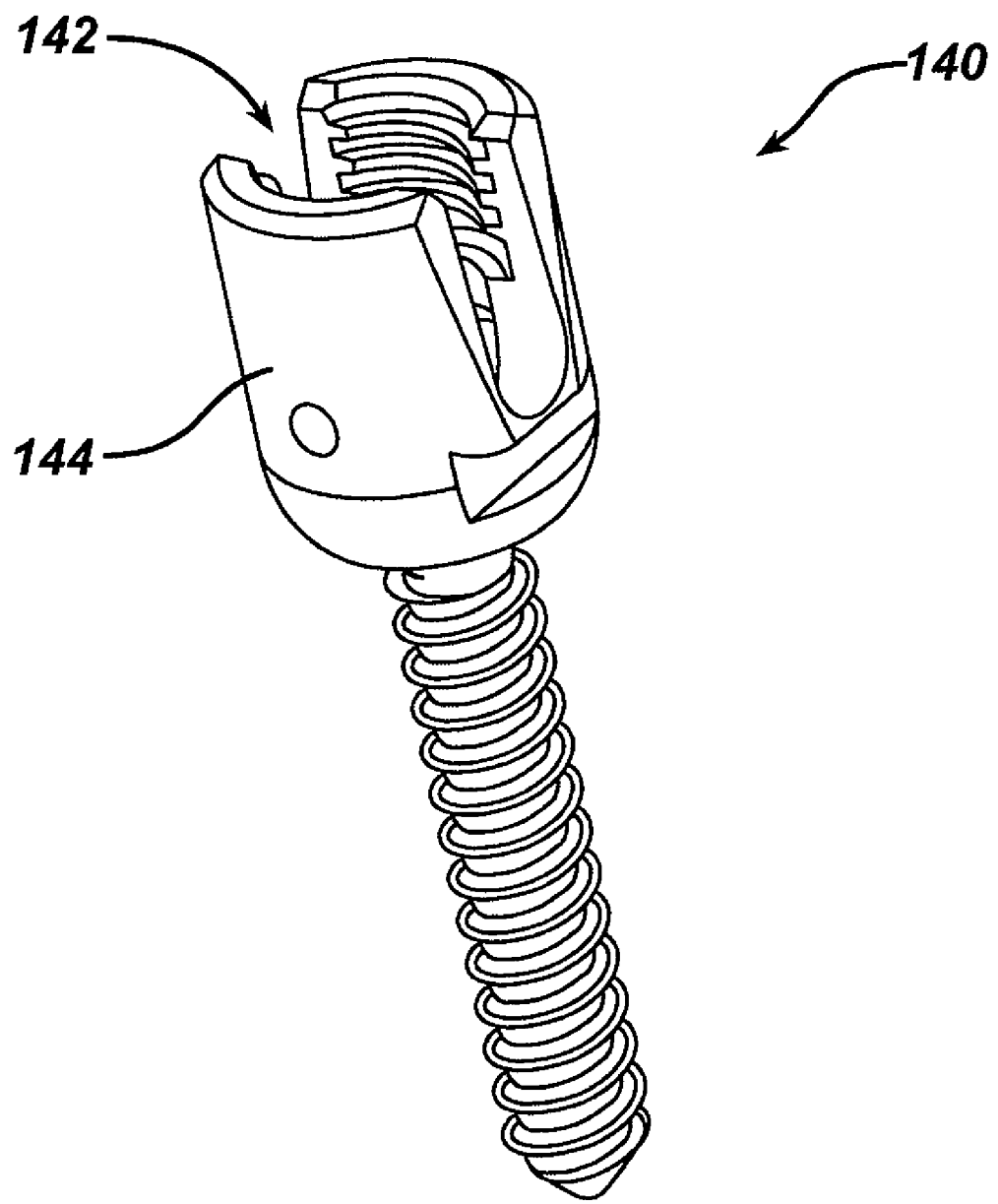
FIG. 14 is a perspective view of one exemplary embodiment of a prior art polyaxial bone screw for use with a spinal stabilization device of the present invention.

As previously indicated, when a spinal stabilization device is implanted, preferably one or more of the arms of the device is mated to a vertebra. While a variety of bone-engaging devices can be used to mate the arm(s) to a vertebra, in one exemplary embodiment a polyaxial bone screw is used. FIG. 14 illustrates one exemplary embodiment of a prior art polyaxial bone screw 140 for use in connecting an arm of a stabilization device to bone, and more preferably to the pedicle of a vertebra. The bone screw 140 can be implanted in the pedicle, and an arm of a device can be positioned within a receiving recess 142 formed in the head 144 of the bone screw 140. A fastening element, such as a locking nut, can then be threaded onto the head 144 of the bone screw 140 to engage the arm. A person skilled in the art will appreciate that a variety of other techniques known in the art can be used to mate the stabilization devices to bone, and FIG. 14 merely illustrates one exemplary embodiment of one such device.

Figure 15A:
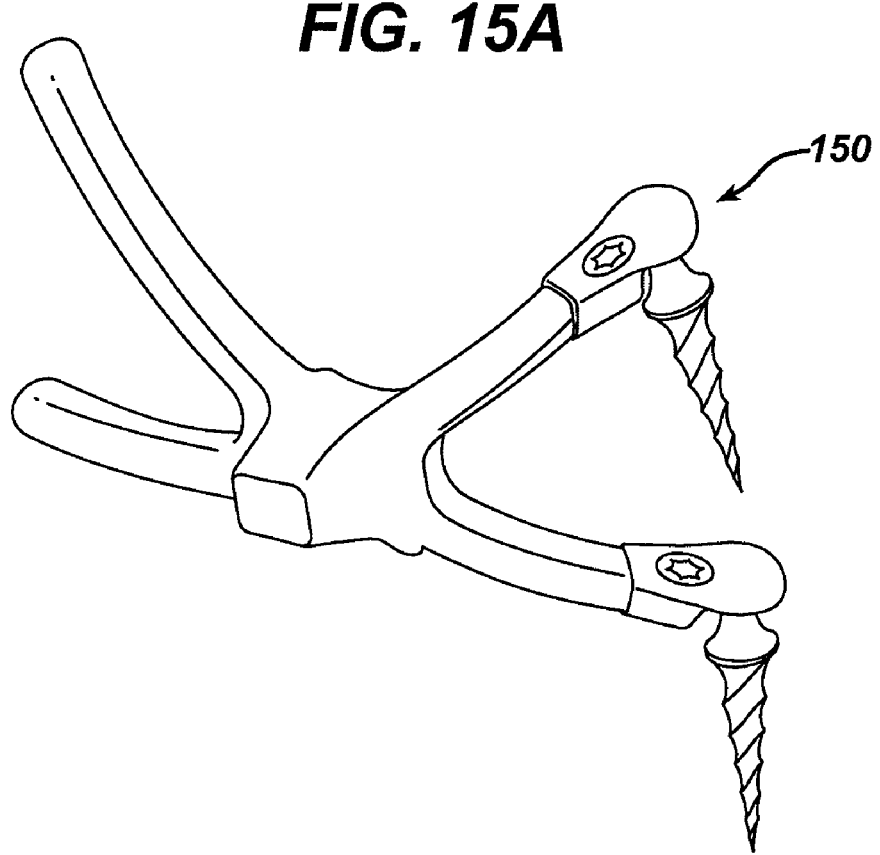
FIG. 15A is a posterior perspective view of one exemplary embodiment of a connector for mating a spinal stabilization device to bone, showing two connectors mated to a terminal end of two of the arms of the device shown in FIG. 1A.
Figure 15B:
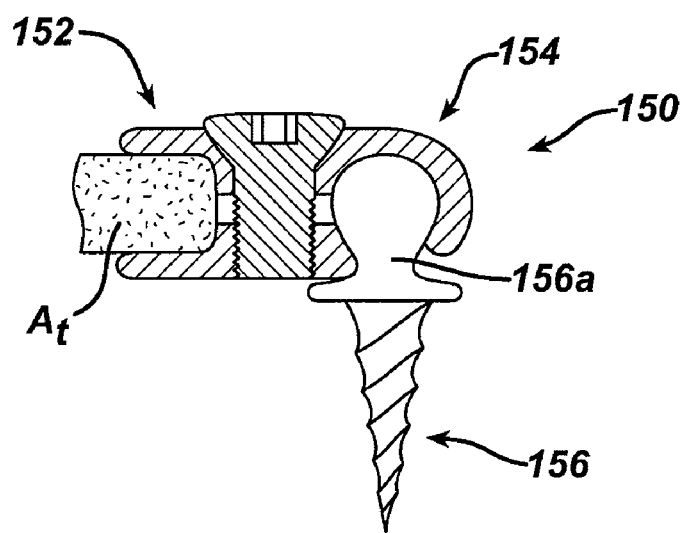
FIG. 15B is a side cross-sectional view of one of the connectors shown in FIG. 15A.

FIGS. 15A and 15B illustrate another exemplary embodiment of a device for mating an arm to bone. In this embodiment, the bone-engaging element 150 is in the form of a clamp have a first end 152 with a cylindrical recess formed therein for receiving a terminal end of an arm $A_t$, and a second end 154 having a spherical recess for receiving a spherical head 156a of a bone screw 156. Such a configuration allows the bone screw 156 to be positioned at a desired angle relative to the arm $A_t$.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A spinal stabilization device, comprising:
   a first pair of arms and a second pair of arms, each pair of arms having a superior portion adapted to mate to a superior vertebra, an inferior portion adapted to mate to an inferior vertebra, and a central portion extending between the superior and inferior portions;
   a central spacer adapted to be positioned between posterior elements of adjacent vertebrae, the central spacer having a central lumen extending laterally therethrough between opposed lateral sides thereof; and
   a cross-connector extending through the central lumen in the central spacer such that opposed ends of the cross-connector extend laterally outward from the opposed lateral sides of the central spacer, the cross-connector having first and second openings formed in the opposed ends thereof that engage the central portion of the first and second pair of arms and a set screw extendable through a bore formed in the cross-connector and configured to cause the cross-connector to engage the central portion of both the first and second pair of arms.

2. The spinal stabilization device of claim 1, wherein the cross-connector is slidably adjustable relative to the first and second pair of arms.

3. The spinal stabilization device of claim 1, wherein the cross-connector includes hook-shaped members formed on the opposed ends thereof that define the first and second openings.

4. The spinal stabilization device of claim 1, wherein the cross-connector is in the form of a clamp for engaging the arms when the clamp is in a closed position.

5. The spinal stabilization device of claim 1, wherein the central spacer is formed from a compressible material and is adapted to limit extension of adjacent vertebrae.

6. The spinal stabilization device of claim 1, wherein the first and second pair of arms each have a unitary configuration and are formed from an elastomeric material with multiple durometers.

7. The spinal stabilization device of claim 1, further comprising a set screw configured to extend through the central spacer and to engage the cross-connector to fixedly mate the central spacer to the cross-connector.

8. The spinal stabilization device of claim 1, wherein the superior and inferior portions of each of the first and second arms extend at an angle relative to the central portion and diverge with respect to one another away from the central portions.

9. A spinal stabilization device, comprising:
   a central spacer having first and second opposed lateral sides, the central spacer being adapted to be positioned between posterior elements of adjacent superior and inferior vertebrae and adapted to limit extension of the adjacent superior and inferior vertebrae;
   a first pair of arms extending from the first lateral side of the central spacer, the first pair of arms being adapted to couple to adjacent superior and inferior vertebrae, and a second pair of arms extending from the second lateral side of the central spacer, the second pair of arms being adapted to couple to adjacent superior and inferior vertebrae, at least one of the first and second pairs of arms having superior and inferior portions that diverge at an obtuse angle with respect to one another; and
   a cross-connector extending through the central spacer and adapted to mate to the first and second pair of arms, the cross-connector including a set screw extendable through a bore formed in the cross-connector and configured to cause the cross-connector to engage both the first and second pair of arms;
   wherein the central spacer is slidably adjustable in a superior-inferior direction relative to the first and second pair of arms.

10. The spinal stabilization device of claim 9, wherein at least a portion of at least one of the first and second pair of arms is pliable for providing resistance to movement of adjacent superior and inferior vertebrae coupled thereto.

11. The spinal stabilization device of claim 9, wherein the first and second pair of arms each have a unitary construction and are formed from an elastomeric material with multiple durometers.

12. The spinal stabilization device of claim 11, wherein the cross-connector is configured to allow slidable adjustment of the central spacer relative to the first and second pair of arms.

13. The spinal stabilization device of claim 12, further comprising a set screw configured to extend through the central spacer and to engage the cross-connector to fixedly mate the central spacer to the cross-connector.

14. The spinal stabilization device of claim 9, wherein the central spacer is compressible.

* * * * *